(12) United States Patent
Martin (10) Patent No.: US 11,504,502 B1
(45) Date of Patent: Nov. 22, 2022

(54) SUCTION CATHETER HOLDER

(71) Applicant: Tomas A. Martin, Boca Raton, FL (US)

(72) Inventor: Tomas A. Martin, Boca Raton, FL (US)

(*) Notice: Subject to any disclaimer, the term of this patent is extended or adjusted under 35 U.S.C. 154(b) by 0 days.

(21) Appl. No.: 17/453,444

(22) Filed: Nov. 3, 2021

(51) Int. Cl.
| | | |
|---|---|---|
| *A61M 25/02* | (2006.01) |
| *A61M 1/00* | (2006.01) |
| *A61B 50/24* | (2016.01) |
| *A61B 50/22* | (2016.01) |
| *A61G 13/10* | (2006.01) |
| *A61C 17/022* | (2006.01) |

(52) U.S. Cl.
CPC .............. *A61M 25/02* (2013.01); *A61B 50/22* (2016.02); *A61B 50/24* (2016.02); *A61C 17/022* (2013.01); *A61G 13/101* (2013.01); *A61M 1/84* (2021.05); *A61M 2025/028* (2013.01); *A61M 2209/084* (2013.01); *Y10S 128/26* (2013.01)

(58) Field of Classification Search
CPC ...... A61B 50/22; A61B 50/24; A61G 13/101; A61M 1/84; A61M 2025/028; A61M 2209/084; A61M 5/1414; A61M 5/1415; A61M 5/1417; A61M 5/1418; Y10S 128/26; Y10S 224/901; Y10S 224/906; Y10S 224/915; Y10S 224/918; Y10S 224/922; Y10S 224/935; A61C 19/00; A61J 1/16; B01L 9/06; B01L 9/065
See application file for complete search history.

(56) References Cited

U.S. PATENT DOCUMENTS

| | | | | |
|---|---|---|---|---|
| 2,020,663 A | * | 11/1935 | Stapleford | B65D 5/72 229/142 |
| 2,202,523 A | * | 5/1940 | Gottheim | B65F 1/08 206/63.5 |
| 3,147,906 A | * | 9/1964 | Roccaforte | B65D 5/16 229/122 |
| 3,166,189 A | * | 1/1965 | Disston | A61M 25/002 206/364 |
| 3,210,816 A | * | 10/1965 | Bette | A61C 19/00 24/570 |

(Continued)

FOREIGN PATENT DOCUMENTS

| | | |
|---|---|---|
| EP | 0125354 | 11/1984 |
| WO | 9728067 | 8/1997 |

*Primary Examiner* — Adam Marcetich
(74) *Attorney, Agent, or Firm* — Nolan IP Law; Jason M. Nolan (57) ABSTRACT

A suction catheter holder is provided. The holder can include a housing that defines an interior open-space compartment for receiving at least a portion of a suction catheter. The housing can have an elongate structure defined by a longitudinal and lateral axis. The housing can include a base panel having a substantially flat exterior surface, and a plurality of sidewalls, each extending upward from the base to a roof panel having an interior surface that faces, at least in part, an interior surface of the base panel. The housing can include a front sidewall panel extending laterally along the front edges of the base and roof panels, between a pair of longitudinal sidewalls. The front sidewall panel can include an insertion through-hole for receiving the suction catheter and a securing through-hole for retaining the suction catheter in place.

18 Claims, 6 Drawing Sheets

(56) References Cited

U.S. PATENT DOCUMENTS

| | | | | |
|---|---|---|---|---|
| 3,494,536 A * | 2/1970 | Henry | | B65D 5/16 |
| | | | | 206/370 |
| 4,006,854 A * | 2/1977 | Gibson | | B65D 85/676 |
| | | | | 229/174 |
| 4,163,372 A * | 8/1979 | Frye | | F25B 41/37 |
| | | | | 62/262 |
| 4,801,294 A * | 1/1989 | Okada | | A61M 25/02 |
| | | | | 604/161 |
| 4,848,575 A * | 7/1989 | Nakamura | | B65D 83/0805 |
| | | | | 383/211 |
| 4,898,586 A | 2/1990 | McDonough | | |
| 5,039,004 A * | 8/1991 | Simpson | | B01L 1/50 |
| | | | | 220/908 |
| 5,065,939 A * | 11/1991 | Boothe | | B65D 5/42 |
| | | | | 229/165 |
| 5,188,242 A * | 2/1993 | Smith | | B25F 5/029 |
| | | | | 248/205.3 |
| 5,301,799 A * | 4/1994 | Gurba, Jr. | | B44D 3/123 |
| | | | | 206/362 |
| 5,323,901 A * | 6/1994 | Outlaw, III | | A61B 50/362 |
| | | | | 206/370 |
| 5,806,822 A | 9/1998 | Schulz | | |
| 5,915,963 A | 6/1999 | Homra | | |
| 6,561,378 B1 * | 5/2003 | Roessler | | B65D 83/08 |
| | | | | 221/45 |
| 6,840,492 B1 * | 1/2005 | Boyne-Aitken | | F16K 7/066 |
| | | | | 604/249 |
| 7,601,001 B1 * | 10/2009 | McCrary | | A61C 17/06 |
| | | | | 206/363 |
| 10,398,886 B2 | 9/2019 | Myers | | |
| 2001/0010110 A1 * | 8/2001 | Matsushima | | A44B 13/0094 |
| | | | | 24/130 |
| 2002/0092816 A1 * | 7/2002 | Kim | | F16L 3/223 |
| | | | | 248/68.1 |
| 2003/0141209 A1 | 7/2003 | Horrell | | |
| 2005/0205450 A1 * | 9/2005 | Leitch | | A61B 50/362 |
| | | | | 206/363 |
| 2006/0096998 A1 * | 5/2006 | Shabashkevich | | A47K 10/421 |
| | | | | 221/45 |
| 2006/0180714 A1 | 8/2006 | Mailhot, Jr. | | |
| 2006/0192064 A1 | 8/2006 | White et al. | | |
| 2008/0319402 A1 * | 12/2008 | Howlett | | A61M 39/287 |
| | | | | 604/250 |
| 2009/0202960 A1 | 8/2009 | White et al. | | |
| 2009/0308823 A1 * | 12/2009 | DiGasbarro | | A61G 7/0524 |
| | | | | 248/314 |
| 2010/0016817 A1 * | 1/2010 | Cadoche Jacobson | | |
| | | | | A61M 1/0001 |
| | | | | 604/323 |
| 2010/0230432 A1 * | 9/2010 | Cardinal | | B65D 83/0852 |
| | | | | 221/281 |
| 2011/0174823 A1 * | 7/2011 | Silva | | A47K 1/09 |
| | | | | 248/110 |
| 2011/0198453 A1 * | 8/2011 | Volk | | A46B 17/02 |
| | | | | 40/672 |
| 2011/0302748 A1 * | 12/2011 | Avelar | | A43C 7/00 |
| | | | | 24/304 |
| 2012/0228323 A1 * | 9/2012 | Fujimoto | | B65D 83/0894 |
| | | | | 221/45 |
| 2015/0126960 A1 | 5/2015 | Rosemore et al. | | |

* cited by examiner

FIG. 7

SUCTION CATHETER HOLDER

FIELD

The present disclosure generally relates to medical equipment, and more particularly to a device for releasably holding and securing an oral suction instrument, and more particularly to a device for releasably holding and securing an oral suction instrument while the user is utilizing the oral suction instrument in an ambulatory environment.

BACKGROUND

Suction instruments, such as a Yankauer suction catheter, are elongate hollow tubes that are used to suction and remove oropharyngeal secretions, congesting fluids, mucus, or other unwanted debris from the oral passageway of a person in order to prevent aspiration. During some emergency situations, such as when a person suffers cardiac arrest, for example, medical professionals are tasked with transporting the ailing person to a hospital. Typically, the person is carried on a stretcher from their initial location to a medical emergency vehicle, such as an ambulance, and then transported to a hospital or other medical care institution. People suffering from cardiac arrest or other conditions are at risk of involuntarily vomiting or otherwise causing fluids and other stomach contents from their oropharynx or gastrointestinal tract to enter their larynx and lower respiratory tract—a condition called pulmonary aspiration. In some cases, pulmonary aspiration can lead to death from asphyxiation.

Emergency medical professionals commonly use suction catheters to remove potential asphyxiants from a patient's oral passageway. During use, particularly after removing the suction catheter from the patient's mouth, the tip of the suction catheter may include residual fluids, stomach contents, or other potential asphyxiants. And while the patient is being transported from their initial location to a medical emergency vehicle and eventually to a medical care institution, the suction catheter may be used multiple times to clear the patient's oral passageway. Existing stretchers and medical emergency vehicles do not have a device for releasably holding and securing a suction catheter during use, so the suction catheter is often stored under the patient's neck to avoid having it contact the ground or otherwise allowing it to become contaminated. As a result, the medical professionals can be exposed to potentially toxic bodily fluids. For the foregoing reasons, there is a need for an improved suction catheter holder, and more particularly for an improved suction catheter holder that is adapted for use in an ambulatory environment.

SUMMARY

In various embodiments, a suction catheter holder is provided. In some embodiments, the suction catheter holder comprises a housing defining an interior open-space compartment configured to receive at least a portion of a suction catheter; the housing having an elongate structure defined by a longitudinal axis and a lateral axis; wherein the housing comprises a base panel having a substantially flat exterior surface; wherein the housing comprises a plurality of sidewalls, each extending upward from the base panel to a roof panel having an interior surface that faces an interior surface of the base panel; wherein the plurality of sidewalls includes a front sidewall panel extending laterally along a front edge of the base panel and a front edge of the roof panel, between a pair of longitudinal sidewalls; and wherein the front sidewall panel comprises an insertion through-hole for receiving the suction catheter and a securing through-hole for retaining the suction catheter in place.

In some embodiments, the exterior surface of the base panel comprises an adhesive material coated thereon.

In some embodiments, the suction catheter holder comprises a housing defining an interior open-space compartment configured to receive at least a portion of a suction catheter; the housing having an elongate structure defined by a longitudinal axis and a lateral axis; wherein the housing comprises a base panel having a substantially flat exterior surface with an adhesive material thereon, and a removable film covering the adhesive material; wherein the housing comprises a plurality of sidewalls, each extending upward from the base panel to a roof panel having an interior surface that faces, at least in part, an interior surface of the base panel; wherein the plurality of sidewalls includes a front sidewall panel extending laterally between a pair of opposing longitudinal sidewalls, and extending along a front edge of the base and roof panels; wherein the front sidewall panel comprises an insertion through-hole for receiving the suction catheter and a securing through-hole for retaining the suction catheter in place; and wherein the insertion through-hole and the securing through-hole are integrated to form a unitary through-hole with two discrete open areas.

It is to be understood that both the foregoing general description and the following detailed description describe various embodiments and are intended to provide an overview or framework for understanding the nature and character of the claimed subject matter. The accompanying drawings are included to provide a further understanding of the various embodiments and are incorporated into and constitute a part of this specification. The drawings illustrate the various embodiments described herein and, together with the description, explain the principles and operations of the claimed subject matter.

BRIEF DESCRIPTION OF THE DRAWINGS

A complete understanding of the present embodiments and the advantages and features thereof will be more readily understood by reference to the following detailed description, appended claims, and accompanying drawings, wherein:

The drawings are not necessarily drawn to scale, and certain features and certain views of the drawings may be shown exaggerated in scale or in schematic in the interest of clarity and conciseness.

DETAILED DESCRIPTION

Reference will now be made in detail to the exemplary embodiment(s), examples of which are illustrated in the accompanying drawings. The description of the embodiments is intended to be read in connection with the accompanying drawings. Whenever possible, the same reference characters will be used throughout the drawings to refer to the same or like parts.

Before describing the exemplary embodiments, it is noted the embodiments reside primarily in combinations of components and procedures related to the apparatus. Accordingly, the apparatus components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

The specific details of the various embodiments described herein are used for demonstration purposes only, and no unnecessary limitation or inferences are to be understood therefrom. Furthermore, as used herein, relative terms such as "horizontal," "vertical," "up," "down," "top," "bottom," and the like, as well as derivatives thereof (e.g., "horizontally," "downwardly," "upwardly," etc.) should be construed to refer to the orientation as then described or as shown in the drawing figure under discussion. These terms are for convenience of description and normally are not intended to require a particular orientation. Terms including "inwardly" versus "outwardly," "longitudinal" versus "lateral" and the like are to be interpreted relative to one another or relative to an axis of elongation, or an axis or center of rotation, as appropriate. Terms concerning attachments, coupling and the like, such as "connected" and "interconnected," refer to a relationship wherein structures are secured or attached to one another either directly or indirectly through intervening structures, as well as both moveable or rigid attachments or relationships, unless expressly described otherwise, and includes terms such as "directly" coupled, secured, etc. The term "operatively coupled" is such an attachment, coupling, or connection that allows the pertinent structures to operate as intended by virtue of that relationship.

In various embodiments, a suction catheter holder is provided. As shown in FIGS. 1-7, in some embodiments the suction catheter holder 100 comprises a housing 101 that defines an interior open-space compartment 140 that is configured to receive at least a portion of the suction catheter SC. In some embodiments, the housing 101 is an enclosure for holding the suction catheter SC in a specific, inserted position, particularly while the suction catheter SC is being used, and more particularly while the suction catheter SC is being used during the transport of a patient from their initial location (e.g., home, work, etc.) to a medical treatment facility (e.g., hospital). In such embodiments, when the suction catheter SC is in the specific inserted position, the user and surrounding area would not be exposed to any contaminants remaining on the surface of the suction catheter after it has been used to treat a patient.

Figure 1:
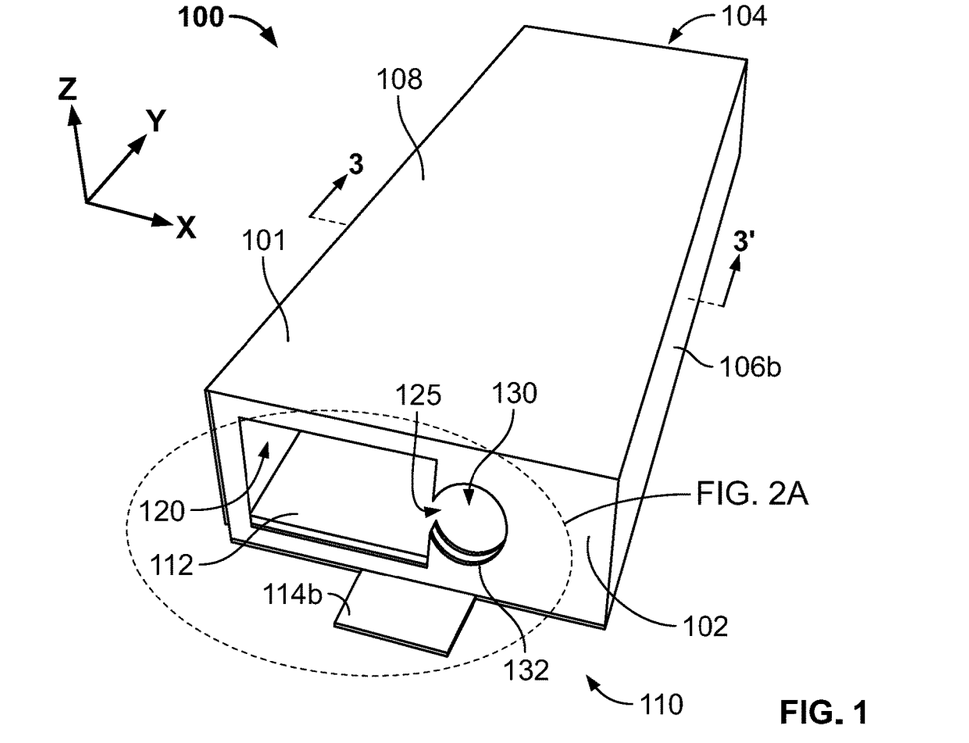
FIG. 1 is a front top perspective view of a suction catheter holder, in accordance with some embodiments described herein.
Figure 5:
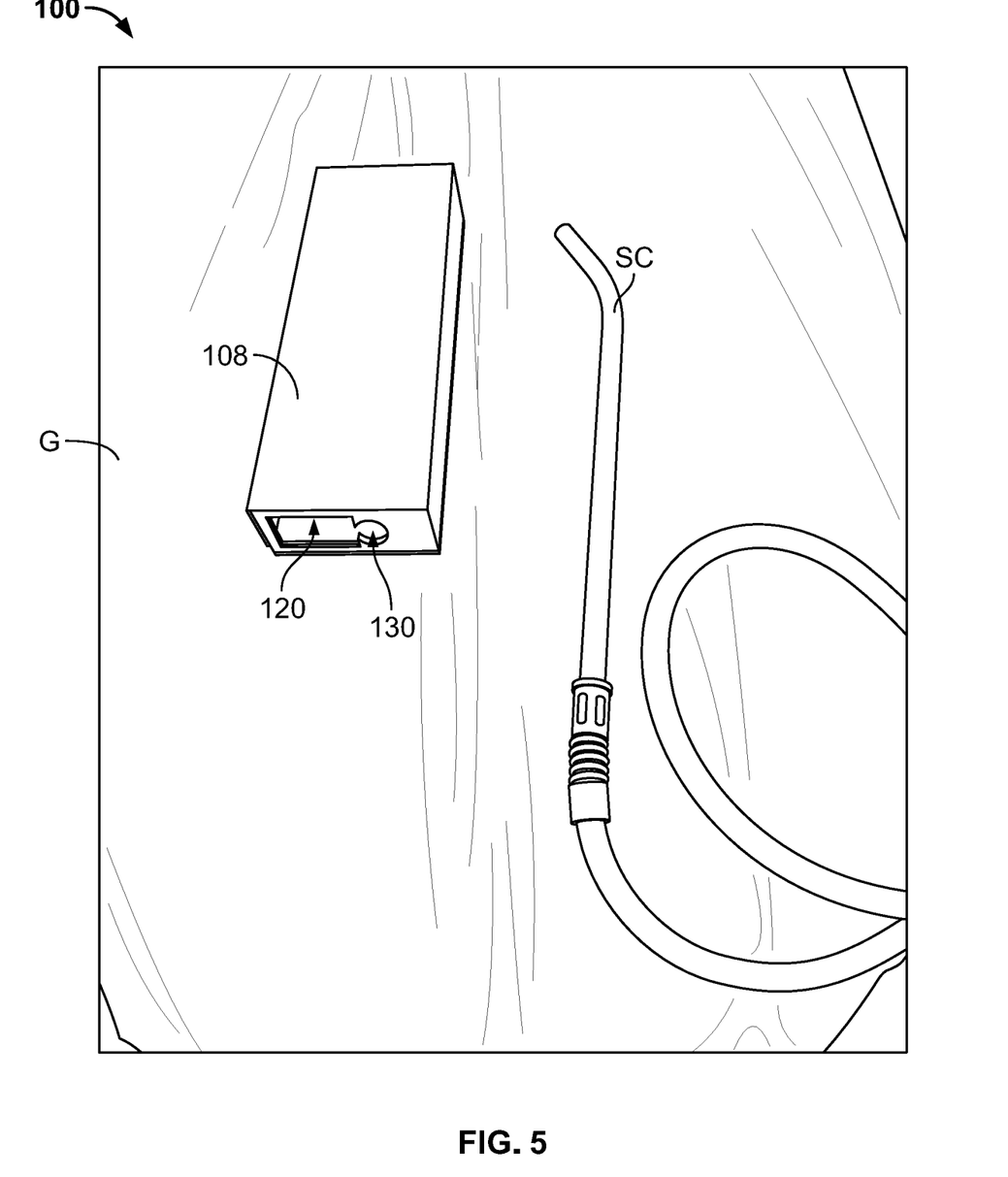
FIG. 5 is a perspective view of the suction catheter holder of FIG. 1 on a patient stretcher along with a suction catheter.

The housing 101 can be any suitable size and have any suitable shape, wherein the suitability is based on the general size and shape of existing and/or commonly used suction catheters. In some embodiments, for example, the housing 101 comprises an elongate structure, with longitudinal and lateral axes, for accommodating the elongate tubing structure of a suction catheter SC. FIG. 1 includes a legend defining the longitudinal axis Y, the lateral axis X, and the vertical axis Z. In some embodiments, the interior compartment 140 defined by the three-dimensional structure of the housing 101 is configured about the longitudinal axis Y having a length that is long enough to receive at least a predetermined portion of the suction catheter SC, a lateral axis X having a width that is wide enough to accommodate the elbow shape of the suction catheter SC, and a vertical axis Z having a height that is high enough to accommodate the diametrical height of the suction catheter SC as well as the features of the front sidewall 102 described herein. FIG. 5, for example, shows the elbow shape of existing and/or commonly used suction catheters.

Figure 6:
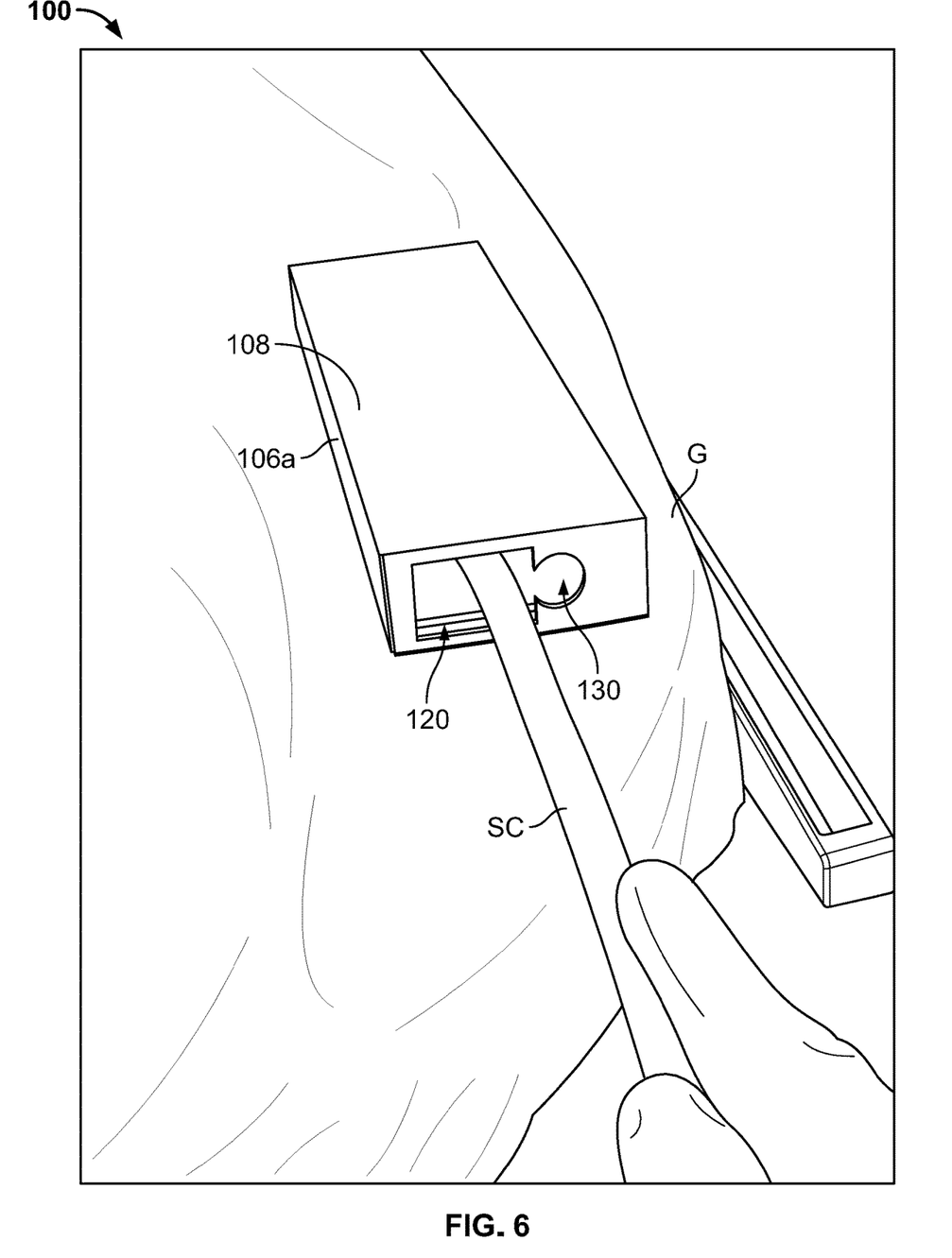
FIG. 6 is a perspective view of the suction catheter holder of FIG. 5 with the suction catheter inserted into the insertion through-hole.
Figure 7:
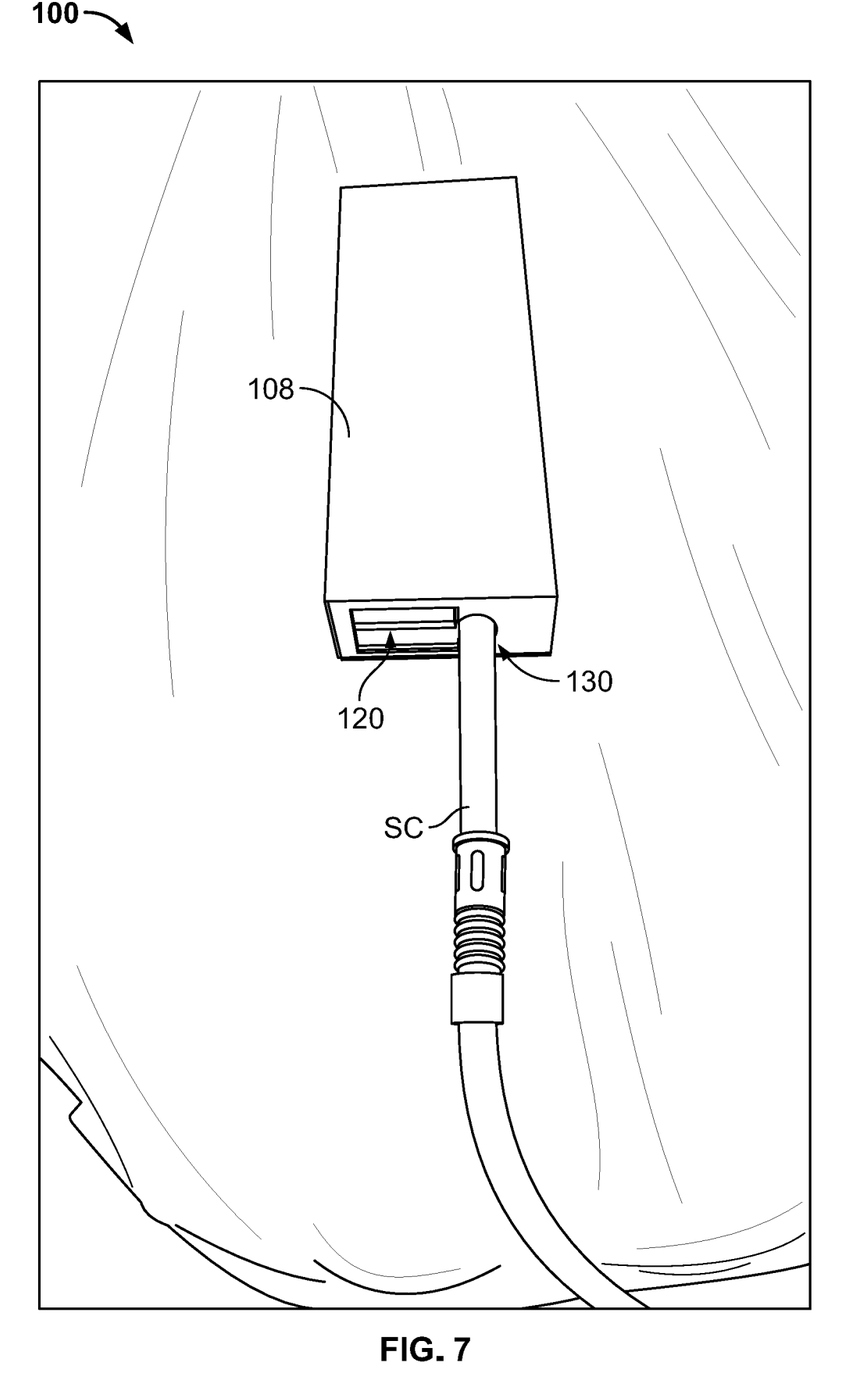
FIG. 7 is a perspective view of the suction catheter holder of FIG. 5 with the suction catheter inserted into the securing through-hole.

In various embodiments, the housing 101 comprises a base panel 110 that is configured to removably lie on the surface of an object, such as the exposed surface area of the gurney G, as shown in FIGS. 5-7. In some embodiments, the base panel 110 comprises a flat or substantially flat exterior surface that is configured to lie and remain in a specific, predetermined position without rolling and/or without sliding on or about the surface (e.g., the linen of the gurney). In some embodiments, the housing 101 comprises a plurality of sidewalls (102, 104, 106a, 106b). In such embodiments, each respective sidewall projects transversely about the vertical axis (e.g., obliquely, upward, vertical, orthogonal, substantially orthogonal, etc.) from the base panel 110 toward and to the roof panel 108. In some embodiments, each sidewall projects transversely about the vertical axis from the outer edges of the base panel 110 toward and to the outer edges of the roof panel 108. In some embodiments, the roof panel 108 has an exterior surface and an opposing interior surface that faces, at least in part, or at least generally, the interior surface of the base panel 110.

In some embodiments, as shown in FIGS. 1-7, the housing 101 comprises a rectangular prism shape. In such embodiments, the base panel 110 and the roof panel 108 have identical, or substantially identical, longitudinal and lateral dimensions and each of their respective interior surfaces face one another. In such embodiments, the base panel 110 and the roof panel 108 are separated by a spaced distance defined by the height of the plurality of sidewalls extending about the vertical axis Z. In some embodiments, each of the sidewalls 106a and 106b extend longitudinally about the longitudinal axis Y, and each of the front and rear sidewalls 102 and 104, respectively, extend laterally about the lateral axis X. In such embodiments, the longitudinal sidewalls 106a, 106b have identical, or substantially identical, dimensions and their respective interior surfaces face one another. In such embodiments, the longitudinal sidewalls 106a, 106b are separated by a spaced distance defined by the width of the base and roof panels 110, 108. In such embodiments, the front and rear sidewalls 102, 104 have identical, or substantially identical, dimensions and their respective interior surfaces face one another. In such embodiments, the front and rear sidewalls 102, 104 are separated by a spaced distance defined by the length of the base and roof panels 110, 108.

Alternative three-dimensional shapes and configurations for the housing 101 are contemplated. For example, in some embodiments the longitudinal sidewalls 106a and 106b and/or the front and rear sidewalls 102 and 104, respectively, can have non-identical (unequal) heights along the vertical axis Z. In another alternative, the front and rear sidewalls 102 and 104 can have non-identical (unequal) lengths about the lateral axis X. In another alternative, the roof panel 108 can have a non-flat configuration, including, for example, an arched, dome shape extending between the longitudinal sidewalls 106a and 106b. In another alternative, the longitudinal sidewalls 106a, 106b and the front and rear sidewalls 102, 104 can define a housing shape and configuration that mimics the long and elbow shape features of a suction catheter so long as there is a flat, or substantially flat, base panel 110 for laying and resting in position on the surface of an object (e.g., gurney).

The housing 101 can be comprised of any suitable material. For example, in some embodiments, the housing 101 is comprised of a paper product, such as corrugated fiberboard. In some embodiments, the corrugated fiberboard comprises a coating, which serves as a moisture and/or vapor barrier to preserve the strength of the material when exposed to wet contents and to prevent liquid from leaking through the housing 101. In some embodiments, the coating is a wax coating or a wax alternative coating. In alternative embodiments, the housing 101 comprises a polymer product, such as a plastic, silicone rubber, or similar material that is moisture- and/or vapor-resistant, or moisture- and/or vapor-proof. In some embodiments, the suction catheter holder 100 is intended to function as a disposable, single-use device. In such embodiments, the suitability of the material for the housing 101 is based on the intended use.

In some embodiments, the housing 101 comprises an adhesive material on the external surface of the base panel 110. Any suitable adhesive material can be used, so long as the material allows a user to removably attach the suction catheter holder 100 to a desired surface (e.g., the linen cloth on a gurney) in a specific, predetermined position. The adhesive material can be applied to the surface of the base panel 110 by any suitable means (e.g., a coating applied via spraying, dispersion, deposition, etc.). In some embodiments, for example, the adhesive material is an acrylate (e.g., methacrylates or epoxy diacrylates) or mixture thereof.

In some embodiments, the suction catheter holder 100 comprises a removeable (e.g., peelable) film 114a that lays over, covers, and protects the adhesive material on the external surface of the base panel 110. In such embodiments, the film 114a is removed from the external surface of the base panel 110 prior to using the suction catheter holder 100. In some embodiments, the film 114a includes a tab 114b to facilitate the removal of the film 114a from the suction catheter holder 100. The film 114a and tab 114b comprise any suitable material. For example, in some embodiments, the film 114a and tab 114b are unitarily or independently comprised of coated paper, plastic sheet, or other materials such as those commonly used as a release liner (e.g., super calendered Kraft paper (SCK), glassine, clay coated Kraft paper (CCK), machine finished Kraft paper (MFK), machine glazed paper (MG), biaxially-oriented polyethylene terephthalate (BO-PET), biaxially-oriented polypropylene (BOPP), or other polyolefins comprising high density polyethylene (HDPE), low density polyethylene (LDPE), or polypropylene resins, or some combination thereof.

In various embodiments, the housing 101 comprises the front panel 102, which extends laterally along the respective front edges of the base panel 110 and the roof panel 108, and between the respective front edges of the longitudinal sidewalls 106a and 106b. In some embodiments, the front panel 102 comprises the insertion through-hole 120, which is configured for receiving the tip and tubing portions of the suction catheter SC, and the securing through-hole 130, which is configured for retaining the tip and tubing portions of the suction catheter SC in a secured position.

As shown in FIGS. 1-7, the housing 101 defines an interior open-space compartment 140 that is configured to receive at least a portion of the suction catheter SC (e.g., the tip portion distal to the elbow and a portion of the shank portion proximal to the elbow). In some embodiments, access to the interior open-space compartment 140 is permitted by the insertion through-hole 120 and/or the securing through-hole 130 on the front sidewall panel 102. In some embodiments, the insertion through-hole 120 is a relatively large opening and the securing through-hole 130 is a relatively small opening. In some embodiments, the relatively large opening provided by the insertion through-hole 120 is advantageous because it does not require the user to precisely aim the tip of the suction catheter when inserting the same. For example, in an emergency situation—such as when an ambulance is moving in transit and the user is restricted as to where she can physically move within the patient cabin of the vehicle, or generally when the user is riding under stressful or difficult driving conditions—the user can easily insert the suction catheter SC into the insertion through-hole 120. After the suction catheter SC has been inserted in the interior open-space compartment 140, it can be moved directly to the securing through-hole 130 via the passage 125 without removing the suction catheter SC from the interior compartment 140. In some embodiments, the suction catheter SC is forcibly moved by the user from the insertion through-hole 120 to the securing through-hole 130 via the passage 125 while a portion of the suction catheter SC remains inside the interior compartment 140. In some embodiments, the passage 125 between the adjacent insertion through-hole 120 and securing through-hole 130 creates a unitary through-hole on the front panel 102. In this context, the unitary through-hole on the front panel 102 comprises a pair of delineated sub-through-holes having a shared edge that is interrupted by the passage 125. In such embodiments, the insertion through-hole and the securing through-hole are integrated to form a unitary through-hole with two discrete open areas.

Figure 2A:
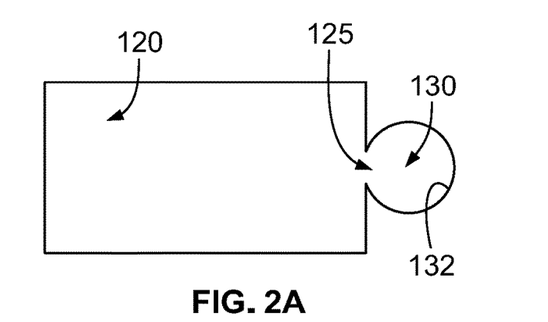
FIG. 2A is a front zoomed-in view of the through-holes circled in the suction catheter holder of FIG. 1.

In various embodiments, the insertion through-hole 120 can have any suitable size and shape. In some embodiments, as shown in FIG. 2A, the insertion through-hole 120 comprises a relatively large rectangular shape. In such embodiments, the rectangular shape includes a pair of edges extending about the lateral axis and a pair of edges extending about the vertical axis. In some embodiments, the insertion through-hole 120 comprises an edge extending about the vertical axis Z that is interrupted by the passage 125. In such embodiments, the passage 125 provides access to the adjacent securing through-hole 130. In some embodiments, the discrete open area defined by the insertion through-hole 120 is larger than the discrete open area defined by the securing through-hole 130.

Figure 2B:
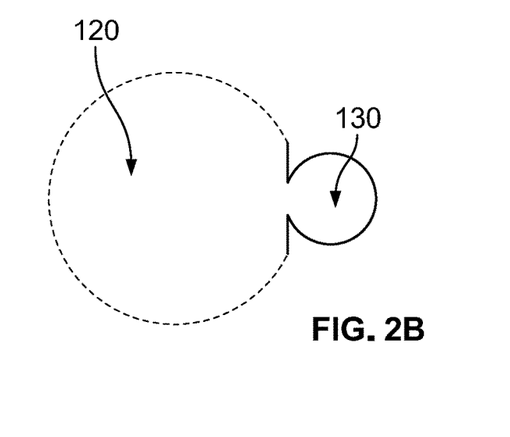
FIG. 2B is a front zoomed-in view of an alternative embodiment of the through-holes of FIG. 2A, in accordance with some embodiments described herein.

Alternative shapes for the insertion through-hole 120 are contemplated. As shown in FIG. 2B, the shape of the insertion through-hole 120 can be any suitable shape. In such embodiments, the shape of the insertion through-hole 120 can be determined based on the alternative three-dimensional shapes and configurations of the housing 101 so long as the insertion through-hole 120 and the securing through-hole 130 are adjacent to one another and share a common edge along the vertical axis Z.

In various embodiments, as shown in FIGS. 1, 2A-2C, 2E, 2F, and 4-7, the securing through-hole 130 comprises a semicircular shape. In this context, "semicircular" refers to an incomplete circle having a circumferential edge that is less than a full circle but more than a half circle. In such embodiments, the semicircular shape is configured to receive and secure a suction catheter SC having a circular cross-sectional shape. In some embodiments, the securing through-hole 130 comprises a diameter that is larger than a diameter of the suction catheter SC. In some embodiments, the securing through-hole 130 comprises a circumferential edge 132 about the circular boundary and further comprises an interruption in the circumferential edge 132 that provides the passage 125. In such embodiments, the passage 125 provides access to the adjacent insertion through-hole 120.

Figure 2C:
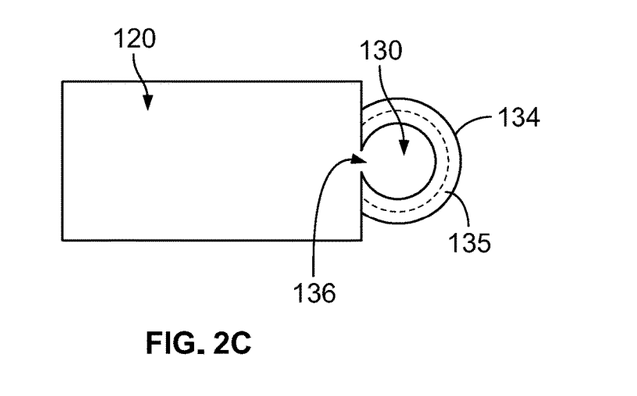
FIG. 2C is a front zoomed-in view of an alternative embodiment of the through-holes of FIG. 2A, with a collar attached to the securing through-hole, in accordance with some embodiments described herein.
Figure 2D:
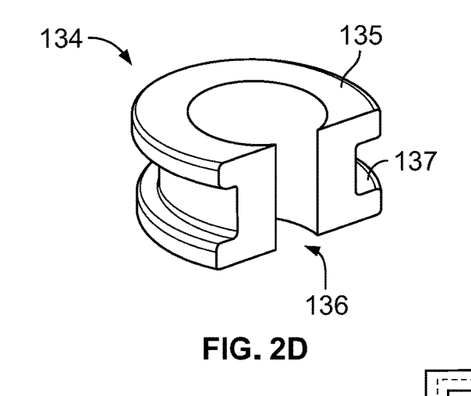
FIG. 2D is a perspective view of the collar shown in FIG. 2C.

In some embodiments, as shown in FIGS. 2C and 2D, the housing 101 comprises a collar 134 along the edge 132 of the securing through-hole 130. The collar 134 can comprise any suitable material (e.g., silicone, plastic, rubber, etc.). In some embodiments, the material of the collar 134 comprises a sufficient friction coefficient for retaining the suction catheter SC in the securing through-hole 130, and a sufficient elasticity for allowing the suction catheter SC to the insertion through-hole 120 with the application of force. In such embodiments, the collar 134 comprises a semicircular shape that is consistent with the semicircular shape of the securing through-hole 130. In such embodiments, the collar 134 comprises a passage 136 that is consistent with the passage 125 between the insertion and securing through-holes 120, 130. In some embodiments, the collar 134 is a grommet having a first flange 135 and a second flange 137 projecting outward from the top and bottom edges, respectively, of a cylindrical structure. In some embodiments, the collar 134 is insertable into the securing through-hole 130 such that the cylindrical structure between the first and second flanges 135, 137 is in contact with the diametrical edge 132 of the securing through-hole 130 and the first and second flanges 135, 137 are in contact with the interior and exterior surfaces of the front panel 102. In alternative embodiments, the second flange 137 can be omitted and the collar 135 comprises a "T" cross-sectional shape. In such embodiments, the collar 134 is insertable (e.g., can be forced, pushed, and/or squeezed) into the securing through-hole 130 such that the cylindrical structure is in contact with the circumferential edge 132 of the securing through-hole 130 and the first flange 135 is in contact with the exterior surface of the front panel 102. In use, the collar 134 provides reinforcing support to the structure of the front panel 102 and particularly to the securing through-hole 130.

Figure 2E:
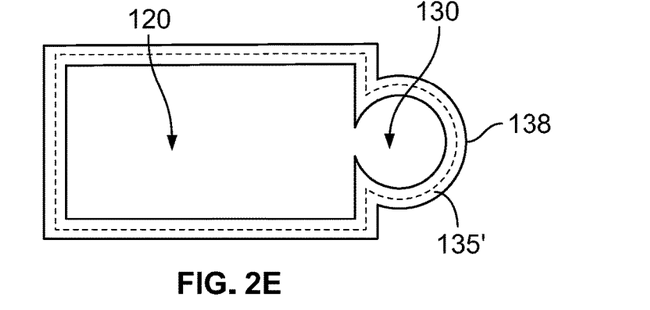
FIG. 2E is a front zoomed-in view of an alternative embodiment of the through-holes of FIG. 2A, with a collar attached to the through-holes, in accordance with some embodiments described herein.
Figure 2F:
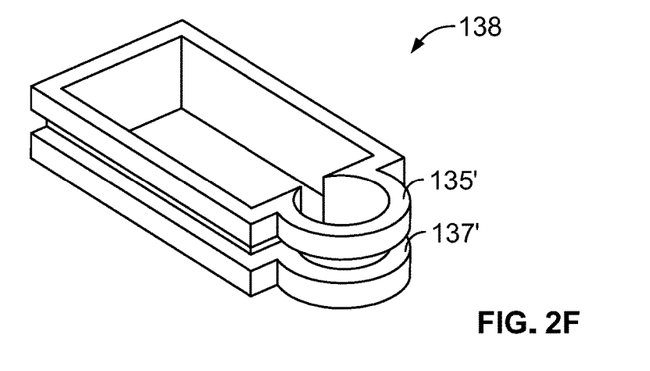
FIG. 2F is a perspective view of the collar shown in FIG. 2E.

In some embodiments, as shown in FIGS. 2E and 2F, the housing 101 comprises a collar 138 lined along the edge of the unitary through-hole comprising the insertion through-hole 120 and the securing through-hole 130. The collar 138 can comprise any suitable material (e.g., silicone, plastic, rubber, etc.). In some embodiments, the collar 138 is a grommet having a first flange 135' and a second flange 137' projecting outward from its core structure. In some embodiments, the collar 138 is insertable into the unitary through-hole such that the core structure between the first and second flanges 135', 137' is in contact with the edge of the unitary through-hole and the first and second flanges 135', 137' are in contact with the interior and exterior surfaces of the front panel 102. In alternative embodiments, the second flange 137' is omitted the collar 138 comprises a "T" cross-sectional shape. In such embodiments, the collar 138 is insertable (e.g., can be forced, pushed, and/or squeezed) into the unitary through-hole comprising the insertion through-hole 120 and the securing through-hole 130 such that the core structure is in contact with the edge of the unitary through-hole and the first flange 135' is in contact with the exterior surface of the front panel 102. In use, the collar 138 provides reinforcing support to the structure of the front panel 102 and particularly to the unitary through-hole comprising the insertion through-hole 120 and the securing through-hole 130.

Figures 3A, 3B:
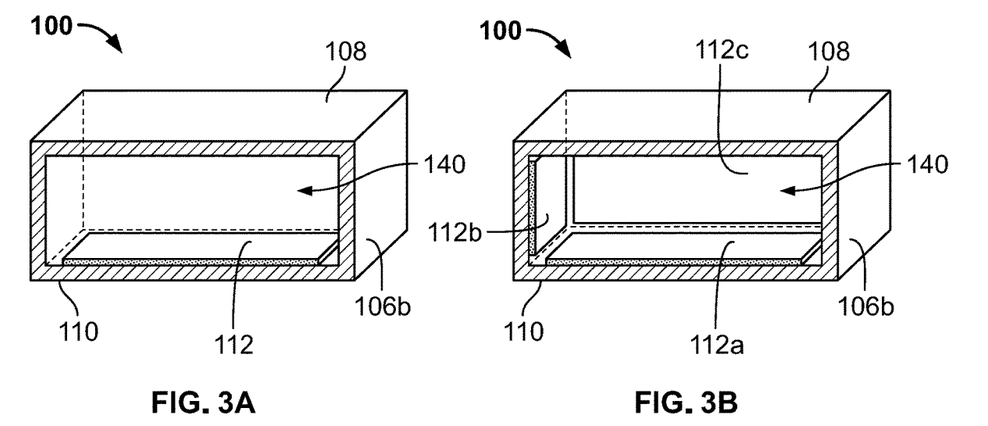
FIG. 3A is a cross-sectional view of the suction catheter holder of FIG. 1, taken along the line labeled 3-3' in FIG. 1.
FIG. 3B is a cross-sectional view of an alternative embodiment of the suction catheter holder of FIG. 1, taken along a line corresponding to the line labeled 3-3' in FIG. 1, in accordance with some embodiments described herein.
Figure 4:
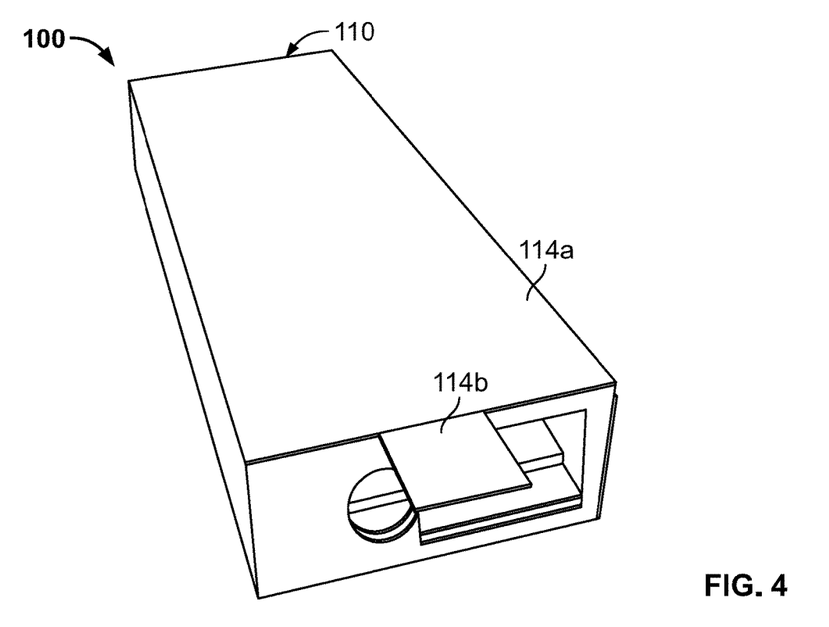
FIG. 4 is a front bottom perspective view of a suction catheter holder of FIG. 1.

In some embodiments, the housing 101 comprises an absorbent pad 112, or a plurality of absorbent pads (e.g., 112a, 112b, 112c, etc.) on one or more surfaces of the interior open-space compartment 140. In some embodiments, as shown in FIGS. 1 and 3A, for example, the interior surface of the base panel 110 is covered with the absorbent pad 112. In some embodiments, the absorbent pad 112 is permanently affixed to the interior surface of the base panel 110. In some embodiments, the absorbent pad 112 is removably attached to the interior surface of the base panel 110. In some embodiments, the housing 101 comprises an absorbent pad 112 on a plurality of surfaces of the interior open-space compartment 140. For example, as shown in FIG. 3B, the housing 101 comprises a plurality of absorbent pad (112a, 112b, 112c, etc.) on each of the plurality of interior surfaces. In some embodiments, the absorbent pad 112 is comprised of a plurality of separate absorbent pads that are individually and collectively configured to cover, or substantially cover, each interior surface of any base and roof panels and any sidewalls facing the interior open-space compartment 140. In some embodiments, the absorbent pad 112 is a single structure that is configured to cover, or substantially cover, the interior surfaces of any base and roof panels and any sidewalls facing the interior open-space compartment 140. In some embodiments, for example, the embodiment shown in FIG. 3B comprising a plurality of individual absorbent pads 112a, 112b, 112c, etc. is modified to an alternative embodiment having an absorbent pad 112 that is a single structure configured to cover the interior surfaces of each of the base and roof panels and each of the sidewalls facing the interior open-space compartment 140.

In use, due to the nature of the suction catheter's utility, some moisture including fluids obtained from the patient's oral cavity can remain in contact with the suction catheter after its removal from the patient's mouth. In some embodiments, the absorbent pad 112 is configured to absorb such fluids and to reduce the moisture remaining on the surfaces of the suction catheter SC after use. The absorbent pad 112 can be any suitable material for absorbing liquid or semi-liquid (e.g., gel) fluids. In some embodiments, the absorbent pad 112 comprises a plurality of layers. In some embodiments, for example, the absorbent pad 112 comprises fibrous materials including paper, gauze, etc., and/or absorbent technologies such as hydrogels. In some embodiments, the absorbent pad 112 comprises medical-grade materials. In some embodiments, the absorbent pad 112 comprises sterile materials. In some embodiments, the absorbent pad 112 comprises an adhesive material on an exterior surface for attaching to the interior surface of the floor panel 110.

The absorbent pad 112 can be any suitable size and shape. The suitability of the size and shape of the absorbent pad 112 is limited only by the ability to function as an absorbent material for fluids. In some embodiments, the absorbent pad 112 comprises a shape that is consistent with the shape of the floor panel 110. For example, if the floor panel 110 has a rectangular shape, then the absorbent pad 112 has a rectangular shape. In some embodiments, the absorbent pad 112 covers at least a portion of the interior surface of the floor panel 110. In some embodiments, the absorbent pad 112 covers the entire interior surface of the floor panel 110. In some embodiments, the absorbent pad 112 comprises a shape that is consistent with the shape of the interior compartment 140 defined by the housing 101.

In some embodiments, the suction catheter holder 100 can comprise a cover for the insertion through-hole 120 and/or the securing through-hole 130 on the front panel 102. In such embodiments, the cover can be removably attached to the housing 101 such that when the user has finished using the suction catheter SC, the insertion through-hole 120 and/or the securing through-hole 130 can be covered to prevent the release or spillage of any fluids or biological materials contained therein.

The suction catheter holder 100 according to the embodiments described herein can be used to removably and securely hold a suction instruction, including existing and commonly used suction catheters. As would be appreciated by one of ordinary skill in the art, the suction catheter 100 is utilized when it is in proximity to the user and the patient. The user utilizes the suction catheter SC one or more times to clear the oral passageway of the patient, and the suction catheter SC is inserted into the suction catheter holder 100 after or in between the one or more times the suction catheter is used to clear the oral passageway of the patient. During use, the user inserts the tip and shank tubing of the suction catheter SC into the interior open-space compartment 140 via the insertion through-hole 120. After insertion, the user slidably moves the suction catheter SC through the passage 125 to the securing through-hole 130, which has a size and shape that restricts the movement of the suction catheter SC. If the user needs to reutilize the suction catheter SC on the patient, then the suction catheter SC is pulled out of the securing through-hole 130 without moving it back to the insertion through-hole 120. Once the user has finished using the suction catheter 100 it can be disposed of.

Exemplary embodiments of the device are described above in detail. The device is not limited to the specific embodiments described herein, but rather, the device may be utilized independently and separately from the other components described herein. For example, the device may also be used in combination with other medical or non-medical instruments and is not limited to its use with the suction catheter SC as described herein. Rather, the exemplary embodiment can be implemented and utilized in connection with other devices.

Although specific features of the present embodiments may be shown in some drawings and not in others, this is for convenience only. In accordance with the principles of the disclosure, any feature of a drawing may be referenced and/or claimed in combination with any feature of any other drawing.

The foregoing is provided for purposes of illustrating, explaining, and describing embodiments of this disclosure. Modifications and adaptations to these embodiments will be apparent to those skilled in the art and may be made without departing from the scope or spirit of this disclosure.

Although the subject matter has been described in terms of exemplary embodiments, it is not limited thereto. Rather, the appended claims should be construed broadly, to include other variants and embodiments, which may be made by those skilled in the art.

I claim:

1. A suction catheter holder, comprising:
a housing defining an interior open-space compartment configured to receive at least a portion of a suction catheter; the housing having an elongate structure defined by a longitudinal axis and a lateral axis;
wherein the housing comprises a base panel;
wherein the housing comprises a plurality of sidewalls, each extending upward from the base panel to a roof panel having an interior surface facing an interior surface of the base panel;
wherein the plurality of sidewalls includes a front sidewall panel extending laterally along a front edge of the base panel and a front edge of the roof panel, between a pair of longitudinal sidewalls;
wherein the front sidewall panel comprises a rectangular shaped insertion through-hole for receiving the suction catheter and a securing through-hole for retaining the suction catheter in place;
wherein the insertion through-hole and the securing through-hole are integrated to form a unitary through-hole with two discrete open areas;
wherein the discrete open area defined by the insertion through-hole is larger than the discrete open area defined by the securing through-hole; and
wherein the discrete open area defined by the insertion through-hole extends laterally across the front sidewall panel from a center portion of the front sidewall to an edge portion proximate to a first respective longitudinal sidewall.

2. The suction catheter holder of claim 1, wherein the unitary through-hole allows the suction catheter to slide between the two discrete open areas without removing the suction catheter from the interior open-space compartment.

3. The suction catheter holder of claim 1, wherein the securing through-hole has a semicircular shape for securing the suction catheter.

4. The suction catheter holder of claim 3, wherein the securing through-hole has a diameter that is larger than a diameter of the suction catheter.

5. The suction catheter holder of claim 1, further comprising a collar extending diametrically around the securing through-hole.

6. The suction catheter holder of claim 5, wherein the collar comprises a sufficient friction coefficient for retaining the suction catheter in the securing through-hole, and a sufficient elasticity for allowing the suction catheter to the insertion through-hole with the application of force.

7. The suction catheter holder of claim 1, further comprising an absorbent pad covering one or more interior surfaces of the interior open-space compartment.

8. The suction catheter holder of claim 1, wherein the base panel comprises a substantially flat exterior surface with an adhesive material coated thereon and a removable film covering the coated exterior surface of the base panel.

9. The suction catheter holder of claim 8, wherein the removable film comprises a tab for assisting the removal of the film from the exterior surface.

10. The suction catheter holder of claim 1, wherein the housing comprises a rectangular prism structure.

11. A suction catheter holder, comprising:
a housing defining an interior open-space compartment configured to receive at least a portion of a suction catheter; the housing having an elongate structure defined by a longitudinal axis and a lateral axis;
wherein the housing comprises a base panel having a substantially flat exterior surface with an adhesive material thereon, and a removable film covering the adhesive material;
wherein the housing comprises a plurality of sidewalls, each extending upward from the base panel to a roof panel having an interior surface facing, at least in part, an interior surface of the base panel;
wherein the plurality of sidewalls includes a front sidewall panel extending laterally between a pair of opposing longitudinal sidewalls, and extending along a front edge of the base and roof panels;
wherein the front sidewall panel comprises a rectangular shaped insertion through-hole for receiving the suction catheter and a securing through-hole for retaining the suction catheter in place; and
wherein the insertion through-hole and the securing through-hole are integrated to form a unitary through-hole with two discrete open areas;
wherein the discrete open area defined by the insertion through-hole is larger than the discrete open area defined by the securing through-hole; and
wherein the discrete open area defined by the insertion through-hole extends laterally across the front sidewall panel from a center portion of the front sidewall to an edge portion proximate to a first respective longitudinal sidewall.

12. The suction catheter holder of claim 11, wherein the unitary through-hole allows the suction catheter to slide between the two discrete open areas without removing the suction catheter from the interior open-space compartment.

13. The suction catheter holder of claim 11, wherein the securing through-hole has a semi-circular shape for securing the suction catheter.

14. The suction catheter holder of claim 13, wherein the securing through-hole has a diameter that is larger than a diameter of the suction catheter.

15. The suction catheter holder of claim 11, further comprising a collar extending diametrically around the securing through-hole.

16. The suction catheter holder of claim 15, wherein the collar comprises a sufficient friction coefficient for retaining the suction catheter in the securing through-hole, and a sufficient elasticity for allowing the suction catheter to the insertion through-hole with the application of force.

17. The suction catheter holder of claim 11, further comprising an absorbent pad covering one or more interior surfaces of the interior open-space compartment.

18. The suction catheter holder of claim 11, wherein the housing comprises a rectangular prism structure.

\* \* \* \* \*